United States Patent [19]
Senninger et al.

[11] Patent Number: 5,344,392
[45] Date of Patent: Sep. 6, 1994

[54] METHOD AND APPARATUS FOR PREPARATION OF SOLUTIONS FROM CONCENTRATES

[75] Inventors: Mark Senninger, Chicago; Rodney Kenley; David Witsoe, both Libertyville, all of Ill.; Richard Bucchianeri, Chelmsford, Mass.; Laura Deming, Lunenburg, Mass.; Ben Garcia, West Roxbury, Mass.

[73] Assignee: Baxter International Inc., Deerfield, Ill.

[21] Appl. No.: 590,420

[22] Filed: Sep. 28, 1990

[51] Int. Cl.$^5$ .................... A61M 1/03; B01D 31/00
[52] U.S. Cl. .......................... 604/4; 604/29; 210/321.71; 210/646
[58] Field of Search ............... 604/4–6, 604/27–31; 210/85, 96.2, 101, 321.71, 647

[56] References Cited

U.S. PATENT DOCUMENTS

| | | | |
|---|---|---|---|
| 4,399,036 | 8/1983 | Babb et al. | 210/321.71 |
| 4,601,830 | 7/1986 | Chen | 210/96.2 |
| 4,739,492 | 4/1988 | Cochran | 210/321.71 |
| 4,814,073 | 3/1989 | Shouldice | 210/321.71 |
| 4,895,657 | 1/1990 | Polaschegg | 210/321.71 |
| 4,897,184 | 1/1990 | Shouldice et al. | 210/96.2 |

FOREIGN PATENT DOCUMENTS

| | | | |
|---|---|---|---|
| 1183461 | 3/1985 | Canada | 604/28 |
| 2924406 | 12/1980 | Fed. Rep. of Germany | 210/647 |
| 3639797 | 2/1988 | Fed. Rep. of Germany | 604/29 |

Primary Examiner—Ralph Lewis
Attorney, Agent, or Firm—Charles R. Mattenson; Thomas S. Borecki; Robert M. Barrett

[57] ABSTRACT

An apparatus for proportioning solutions from at least first and second constituent solutions connected to separate inlet ports of the apparatus first detects which constituent solution is being supplied to which port and then properly proportions the finished solution from the constituent solutions irrespective of which constituent solution is connected to which inlet port.

25 Claims, 1 Drawing Sheet

METHOD AND APPARATUS FOR PREPARATION OF SOLUTIONS FROM CONCENTRATES

TECHNICAL FIELD OF THE INVENTION

This invention relates to the field of solution compounding. More specifically, it relates to an apparatus for compounding finished solutions from two or more constituent solutions particularly for use as a kidney dialysis solution.

BACKGROUND OF THE INVENTION

In the medical field alone, huge volumes of solutions are used everyday for uses such as wound irrigation, intravenous administrations, kidney dialysis, etc. Because of the problems inherent in the use of such large volumes of fluids, such as shipping, handling and storage, as well as sterile concerns, which tremendously complicate the other concerns, concentrates are often prepared which contain some or all of the non-liquid constituents of the finished solution. The concentrates are then diluted or proportioned with the appropriate liquid base, generally water, as close in time to the actual use of the solution as is practical. How close in time to actual use a finished solution may be proportioned is affected by a number of factors such as shelf-life of both the concentrate and the finished solution, various sterilization concerns, shipping and storing concerns, etc.

In the treatment of patients suffering acute or chronic renal insufficiency, dialysis therapy is employed. The two general categories of dialysis therapy are hemodialysis and peritoneal dialysis. In hemodialysis, the patient's blood is cleansed by passage through an artificial kidney in an extracorporeal membrane system. In peritoneal dialysis, dialysis fluid is infused into the patient's peritoneal cavity. This cavity is lined by the peritoneal membrane which is highly vascularized. The metabolites are removed from the patient's blood by diffusion across the peritoneal membrane into the dialysis solution. Excess fluid, i.e. water is also removed by osmosis induced by a hypertonic dialysis solution.

Peritoneal dialysis generally requires large volumes of dialyzing solution. Generally, at each application, or exchange, a given patient will infuse 2 to 3 liters of dialyzing solution into the peritoneal cavity. The solution is allowed to dwell for approximately 3-4 hours, at which time it is drained out and exchanged for fresh solution. Generally, four such exchanges are performed daily. Therefore, approximately 8 to 10 liters of dialyzing solution is required per day, 7 days a week, 365 days a year for each patient.

Dialysis solutions have traditionally been provided in sealed, sterilized form, ready for use. However, several substantial problems become immediately apparent. Shipping and storage of the sheer volume of fluids required is both tremendously inconvenient and expensive. Further, the repeated connection and disconnection of so many solution containers creates a very substantial risk of biological contamination at the point of connection. Additionally, tremendous amounts of waste material, in the form of empty containers and packaging, and their proper disposal are increasingly becoming matters of universal concern.

The traditional response to these problems is to use small volumes of concentrated dialysis solutions diluted with ultra pure water at the point of use. Generally, such concentrates are separated into (1) concentrated solutions containing the various appropriate electrolytes and a buffer and (2) concentrated solutions containing dextrose or another appropriate osmotic agent. The various reasons for separating the dialysis solution into two separate concentrates are well known in the art and include a number of concerns relating to sterilization.

The compounding or proportioning of the concentrates with ultra pure water back into a finished, ready to use dialysis solution are generally performed by machine. Such machines require that the user attach the source of each concentrate to a particular inlet port on the proportioning apparatus, which may be integrated into the dialysis machine itself. Generally, if the concentrates are connected to the wrong ports, or improperly connected, or one or the other not connected at all, the machine will either produce incorrectly proportioned dialysis solution or will alarm.

One such prior art apparatus is disclosed in European publication number 311,848; filed Sep. 29, 1988 in the name of Fresenius Ag. The publication disclosed a hemodialysis machine incorporating a mixing arrangement which produces dialyzing fluid by mixing a concentrate with prepared water. The mixing arrangement employs a protective system independent of the mixing system which is based upon monitoring of the conductivity of the dialyzing fluid. The disclosed system employs conductivity measuring cells placed in the concentrate inlet lines to measure the conductivity of the concentrate coming into the machine and compare it with desired values of the conductivity of concentrates to be connected. In this way, the machine will "identify" if the appropriate concentrate is connected to the appropriate inlet port. If the wrong concentrate is attached to the machine or if two concentrate containers with different concentrates are incorrectly interchanged and each connected to the inlet port designated for the other, the mistake will be sensed and the machine will alarm. Coincidentally, the sensors disclosed in the publication also act as filling level sensors.

The primary problem with such a system is that it still requires that each concentrate be connected only to a particular inlet port of the dialysis machine. Therefore, the requirement for more complicated design, and hence more complicated manufacturing, remains because the appropriate inlet port for each concentrate must be somehow identified, color coded, or even uniquely designed to nave a different shape or configuration from the other inlet port. While this prior art system may provide some increased measure of safety in avoiding improperly prepared dialysis solution, it does nothing to facilitate and simplify the proper connection of concentrates in the first place.

Moreover, automated peritoneal dialysis machines are increasingly being used by the dialysis patients themselves in their own homes to effect multiple exchanges of dialysis solutions into and out of their own peritoneal cavities, generally overnight. The individual patient/operator does not have the training and sophistication with the apparatus which is possessed by the nurse or technician. It is not uncommon for them to become confused when faced with complex machinery, particularly that one upon which their very life depends.

Further, while warnings in the event of improper attachment are vital, dialysis patients are often generally quite physically debilitated. These patients often suffer from inter alia, decreased strength and fine motor control in their hands making proper connection of the concentrate solutions, let alone repeated disconnection and reconnection of improper connections, much more difficult than for the trained professional. Their vision is often impaired, further contributing to the likelihood of improper connections.

What is needed is an improved apparatus that will accept the connection of each concentrate at any concentrate inlet port and still properly proportion the finished dialysis solution.

SUMMARY OF THE INVENTION

The present invention provides an apparatus for compounding solutions from two or more constituent concentrates and water. The apparatus automatically identifies which concentrate is connected to each inlet port of the apparatus and then automatically compounds or proportions the finished solution properly from the concentrates and water irrespective of the inlet port to which each concentrate is connected.

In the case of the automated generation of solutions for kidney dialysis, concentrates are commonly employed which have either a nearly zero or relatively high conductivity. The solutions can be attached to the inlet ports of the compounding apparatus in any sequence and to any inlet port. The apparatus separately senses the conductivity of each of the concentrates and compares each to known values. Based on the information collected, the compounding apparatus proceeds to properly proportion the finished dialysis solution from the two concentrates and a source of water.

The present invention frees the patient from the responsibility of ensuring that the correct constituent concentrate is attached to a specific apparatus inlet port. Allowing such random attachment for the first time in the art is particularly advantageous for the patients and especially those who are visually impaired. The patient is not only protected from connecting the wrong concentrate to the wrong port, but, even more importantly, for the first time the machine is designed to be far more mistake proof by accepting random connection of concentrates.

Instrument design and manufacture is significantly simplified. For example, the need for the concentrate inlet ports to be uniquely configured, color coded, or otherwise differentiated from one another to identify which concentrate must be connected to which port, as is common in prior art designs, is completely negated. Furthermore, the patient is also protected from connecting two of the same concentrates to the ports or forgetting to connect one or both.

DESCRIPTION OF THE PREFERRED EMBODIMENTS

Figure 1:
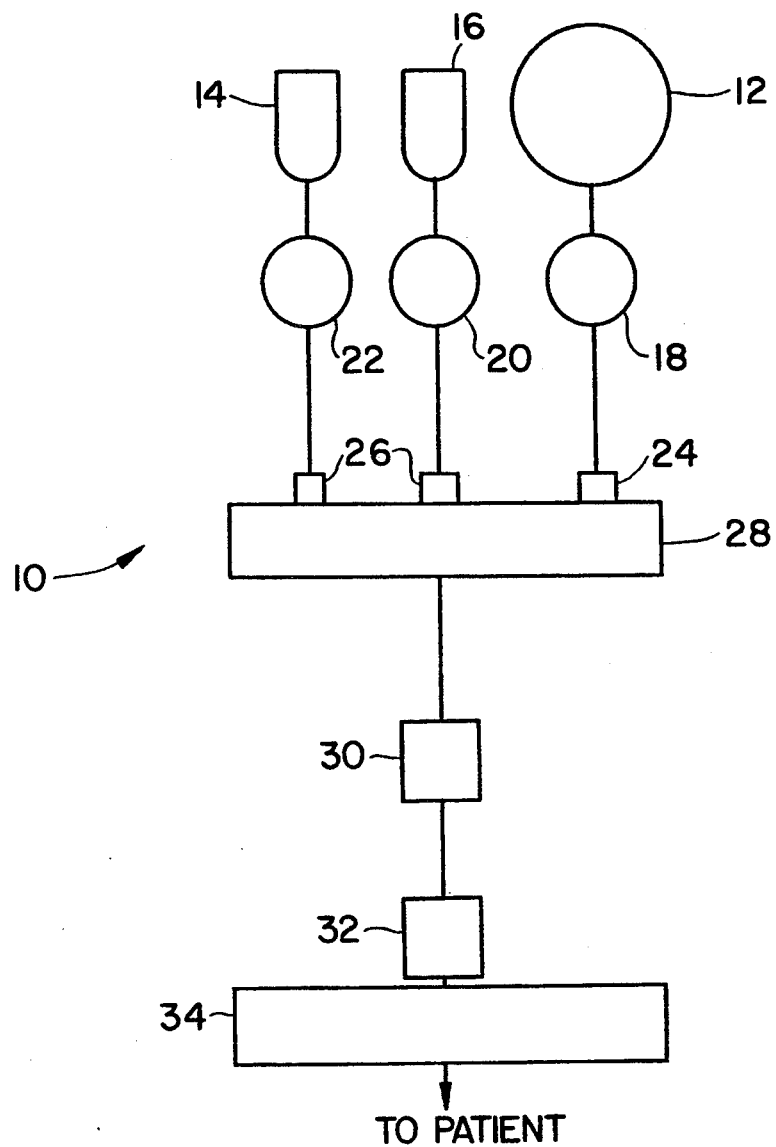
FIG. 1 is a schematic representation of a proportioning apparatus according to the invention.

The present invention provides an apparatus for compounding or proportioning a finished solution from at least two concentrates and water. It is designed to allow connection of each of the concentrates in any order and to any inlet port on the apparatus. The invention will be described below in the context of a system particularly adapted to prepare a finished solution for peritoneal dialysis from two concentrates and sterile water. It will be appreciated that this is to be considered a preferred embodiment only and not limiting to the scope of the invention. The invention is equally applicable and readily adaptable to compounding other types of solutions for use within and without the medical field and to such solutions whether they be compounded from two or more concentrates.

Referring now to FIG. 1, there is represented a schematic diagram of the apparatus 10 of the present invention. Apparatus 10 includes a source of water 12 and sources 14 and 16 of at least two concentrates from which, with the addition of water from source 12, the final solution will be compounded. For purposes of the present discussion, the final solution to be compounded will be a peritoneal dialysis solution as supplied by Baxter Healthcare Corporation, Deerfield, Ill. under the designation PD-1. Baxter's PD-1 solution is formulated from two concentrates having the following compositions.

Concentrate 1

11.34 g/100 ml Sodium Chloride
7.84 g/100 ml Sodium Lactate
514 mg/100 ml Calcium Chloride
304 mg/100 ml Magnesium Chloride adjusted to a pH of approximately 6.4

Concentrate 2

50% dextrose

Each of the concentrates is prepared to require dilution of approximately 1 to 20, i.e. 1 part concentrate to 19 parts water, for preparation of the finished solution. The relative amounts of each of the two concentrates will be adjusted depending upon the desired dextrose composition of the finished solution. For example, if a finished solution containing 2.5% dextrose is desired, equal parts of the two concentrates would be used. One of skill in the art will readily appreciate how to adjust the relative amounts of each of two concentrates to be mixed and then diluted with water to arrive at the desired composition of the finished solution.

Water source 12 preferably may be a direct plumbing connection with in line equipment for sterilizing the water, such as by reverse osmosis, or any other type of water source appropriate to the particular application. The two concentrate sources 14 and 16 may take any convenient and appropriate form such as two liter or larger containers of any particular desired diluent.

Each of water source 12 and concentrate sources 14 and 16 are connected through valves 18, 20 and 22 respectively to water inlet port 24, and concentrate inlet ports 26 of the proportioner 28. It is intended that concentrate inlet ports 26 will be identical to one another so that either of concentrate sources 14 or 16 may be connected to either of concentrate inlet ports 26. Additionally, the apparatus may include more than two inlet ports if the apparatus is to be used to proportion a solution from more than two concentrates.

Two detectors 30 and 32 are located downstream of the proportioner 28 and between the proportioner 28 and the dialysis apparatus 34 which ultimately delivers the finished solution to the patient. In the preferred embodiment, detectors 30 and 32 are conductivity cells and proportioner 28 includes a microprocessor with sufficient capacity to store reference conductivity values for each concentrate and the finished solution as well as software to control all automated functions of the apparatus 10. The inventors have found that a conductivity cell supplied by Thornton Associates, Waltham, Mass. under part number 212-4-01, series 212 works well in this application.

In true operation of true apparatus 10, a sample from first one concentrate source is collected by the apparatus, mixed with water and then pumped past first conductivity cell 30. The conductivity is sensed, compared to the reference values, and if found to be within acceptable parameters, stored in microprocessor's random access memory along with the identification of the inlet port to which it is connected. Next the conductivity cell 30 flushed with purified water. Next, a sample from the other concentrate source is collected by the apparatus, mixed with water and then pumped past the first conductivity cell 30. The conductivity is sensed, compared to the reference values for the other concentrate, and if found to be within acceptable parameters, stored along with the identification of the inlet port to which it is connected.

In the preferred embodiment, the electrolyte concentrate exhibits a very nigh conductivity. The dextrose concentrate exhibits virtually zero conductivity. Thus, the instrument looks for one sample batch with a near zero conductivity and the other with a high conductivity. As noted above, the particular inlet port associated with each conductivity is also stored.

If concentrate solutions of the proper conductivities are sensed, the identities of the concentrates by their respective conductivities are assigned by the apparatus to the respective inlet ports from which each was obtained and stored in RAM to ensure proper proportioning of the finished solution for the duration of that particular dialysis treatment session. The machine then proceeds to prepare batches from each concentrate in predetermined volumes as needed and mix them together in the proportioner 28 to form a finished, ready-to-use peritoneal dialysis solution.

Measurement of any combination of conductivities other than as predetermined, such as the high and near zero values designated in this embodiment, would result in the machine sounding an alarm and failing to prepare and deliver finished solution to the patient. Detection of such a combination of conductivities would mean that either identical solutions were connected to each inlet or only one concentrate was connected to an inlet. The patient/operator would be instructed in correcting the problem such as via a message display.

It should be noted that in the preferred embodiment, not only are the conductivities of each of the test batches measured and compared to reference values, but the conductivity of the finished solution is also monitored as the solution leaves proportioner 28. Further, as illustrated in FIG. 1, in the preferred embodiment a second conductivity cell 32 is included downstream of first cell 30. The second cell 32 is employed as a safeguard against problems due to deterioration of first cell 30. The output of each cell is preferably monitored continuously and checked against each other and the reference values stored in the microprocessor.

In the preferred embodiment, apparatus 10 is intended to be included in an apparatus for performing peritoneal dialysis. However, a proportioning apparatus such as described above could be incorporated into a hemodialysis machine, other type of fluid handling apparatus, or even employed as a stand alone device to generate properly proportioned fluids from concentrates for a broad range of applications.

The invention may be practiced other than precisely as described without departing from the spirit and scope of the invention as claimed. For example, a number of well known types of detectors or sensors could be substituted for the preferred conductivity cells as appropriate and such substitution would be well within the knowledge of one of ordinary skill in the art.

Among those sensors which might be considered appropriate for a given application and which could be readily substituted for conductivity cells are pH sensors, ion-specific field effect transistors, and infra red, soft neutron, ultrasonic, and ultra violet spectroscopic sensors. One of skill in the art could also employ nuclear magnetic resonance to sense an appropriate characteristic of a given concentrate. The choice of sensor is not limited by the invention and one of ordinary skill in the art will readily appreciate how to apply other sensors. The choice of sensor might be dictated by, inter alia, whether the particular concentrates being proportioned are best detected by chemical, optical, electrical or nuclear means.

What is claimed to be protected by Letters Patent of the United States is:

1. An apparatus for proportioning solutions from water and at least first and second concentrates comprising,
   a. proportioning apparatus having at least first and second inlet ports;
   b. means for supplying water to said apparatus;
   c. at least one source of said first concentrate in fluid connection with said first inlet port and at least one source of said second concentrate in fluid connection with said second inlet port;
   d. means for separately determining which concentrate is supplied to each of said inlet ports and adapting said apparatus to properly compound said solution according to predetermined parameters from said concentrates and said water irrespective of the particular inlet port to which each said concentrate is connected from said respective sources.

2. The apparatus of claim 1 wherein said determining means includes means for determining the conductivity of each of said concentrates entering each of said inlet ports.

3. The apparatus of claim 2 wherein said determining means further includes means for comparing said conductivities to predetermined conductivities.

4. The apparatus of claim 1 wherein said determining means includes means for determining the pH of each of said concentrates.

5. The apparatus of claim 4 wherein said determining means further includes means for comparing each said pH against to predetermined values for each pH.

6. An apparatus for proportioning finished solutions from at least first and second constituent solutions, said first constituent solution having a low conductivity and said second constituent solution having a high conductivity, said apparatus comprising,
   a. a compounding apparatus having at least first and second inlet ports;
   b. a first source of said first constituent solution in fluid connection with said first inlet port and a second source of said second constituent solution in fluid connection with said second inlet port;
   d. means for separately detecting which solution is supplied to each of said inlet ports and adapting said machine to properly proportion said finished solution according to predetermined parameters from said first and second constituent solutions irrespective of the particular inlet port to which each is supplied from said respective sources.

7. The apparatus of claim 6 wherein said detecting means includes means for detecting the conductivity of each of said constituent solutions entering each of said inlet ports.

8. The apparatus of claim 7 wherein said detecting means includes means for comparing said conductivities to predetermined conductivities.

9. The apparatus of claim 6 wherein said detecting means includes means for detecting the pH of said constituent solutions.

10. The apparatus of claim 9 wherein said detecting means further includes means for comparing each said pH to predetermined values for each pH.

11. An apparatus for proportioning dialysis solutions from water and at least first and second concentrates comprising,
   a. a proportioning machine having at least first and second inlet ports;
   b. at least one source of water connected to said apparatus;
   c. a least one source of said first concentrate in fluid connection with said first inlet port and at least one source of said second concentrate in fluid connection with said second inlet port;
   d. means for separately detecting which concentrate is supplied to each of said inlet ports and adapting said apparatus to properly proportion said solution from said concentrates and said water irrespective of the particular inlet port to which each is connected from said respective sources, 12. The apparatus of claim 11 wherein said detecting means includes means for detecting the conductivity of each said concentrate entering each of said inlet ports.

13. The apparatus of claim 12 wherein said detecting means includes means for comparing said conductivities to predetermined conductivities.

14. The apparatus of claim 11 wherein said detecting means includes means for detecting the pH of concentrates entering each of said inlet ports.

15. The apparatus of claim 14 wherein said detecting means further includes means for comparing each said pH to predetermined values for each pH.

16. In a dialysis machine having multiple inlet ports and means for proportioning dialysis solutions from at least two concentrates and water supplied to different of said inlet ports, the improvement comprising in combination;
   means for detecting which concentrate is supplied to each said inlet port and for automatically adapting said machine to properly proportion said solutions from said concentrates and said water regardless of which concentrate is supplied to which inlet port.

17. The dialysis machine of claim 16 wherein said detecting means includes means for separately detecting the conductivity of each said concentrate entering each of said inlet ports and comparing said conductivities to predetermined conductivities.

18. The dialysis machine of claim 17 wherein said detecting means includes means for separately determining the pH of each said concentrate entering each of said inlet ports and comparing each said pH to predetermined pH values.

19. A method for proportioning dialysis solutions from water and at least first and second concentrates comprising the steps of:
   providing a source of water;
   providing a source of first concentrate;
   providing a source of second concentrate;
   coupling the source of water to a water inlet of a proportioning apparatus that also includes at least first and second inlets;
   coupling the first source of first concentrate to either the first inlet or the second inlet;
   coupling the second source of second concentrate to the other inlet;
   determining automatically which concentrate is coupled to which inlet; and
   causing the proportioning apparatus to properly compound a solution, according to predetermined parameters, from the concentrates and the water irrespective of the inlet port to which the concentrates are connected.

20. The method of claim 19 including the step of determining the conductivity of each of the concentrates entering the inlet ports.

21. The method of claim 20 including the step of comparing the conductivities to predetermined conductivities.

22. The method of claim 19 including the step of determining the pH of each of the concentrates.

23. The method of claim 22 including the step of comparing the pH's of each of the concentrates against predetermined values.

24. A method of providing dialysis to a patient comprising the steps of:
   providing a dialysis machine having multiple inlet ports and means for proportioning dialysis solutions from at least two concentrates and water supplied to different of said inlet ports;
   allowing the dialysis machine to automatically detect which of the at least two concentrates is supplied to each of the inlets; and
   automatically adapting the machine to properly proportion the solutions from said concentrates and said water regardless of which concentrate is supplied to which inlet port.

25. A method of providing dialysis to a patient comprising the steps of:
   providing a dialysis machine having multiple inlet ports and means for proportioning dialysis solutions from at least two concentrates and water supplied to different of said inlet ports;
   allowing the patient to couple the at least two concentrates to either of at least two inlet ports;
   allowing the dialysis machine to automatically detect which of the at least two concentrates is supplied to each of the inlet ports; and
   automatically adapting the machine to properly proportion the solutions from said concentrates and said water regardless of which concentrate is supplied to which inlet port.

* * * * *